United States Patent
Nakasone et al.

(10) Patent No.: US 10,101,294 B2
(45) Date of Patent: Oct. 16, 2018

(54) METHOD OF RECOVERING PROCESS FOR GAS SENSOR

(71) Applicant: NGK INSULATORS, LTD., Nagoya-shi, Aichi (JP)

(72) Inventors: Osamu Nakasone, Inabe (JP); Noriko Hirata, Nagoya (JP); Takayuki Sakurai, Kakamigahara (JP)

(73) Assignee: NGK INSULATORS, LTD., Nagoya (JP)

( * ) Notice: Subject to any disclaimer, the term of this patent is extended or adjusted under 35 U.S.C. 154(b) by 234 days.

(21) Appl. No.: 15/245,333

(22) Filed: Aug. 24, 2016

(65) Prior Publication Data

US 2017/0059510 A1 Mar. 2, 2017

(30) Foreign Application Priority Data

Aug. 27, 2015 (JP) .................................. 2015-167562
Aug. 18, 2016 (JP) .................................. 2016-160476

(51) Int. Cl.
*G01N 27/406* (2006.01)
*G01N 27/407* (2006.01)
*G01N 27/416* (2006.01)

(52) U.S. Cl.
CPC .............................. *G01N 27/4067* (2013.01)

(58) Field of Classification Search
CPC ........... G01N 27/4067; G01N 27/4075; G01N 27/4074; G01N 27/4163
USPC .......................................................... 219/209
See application file for complete search history.

(56) References Cited

U.S. PATENT DOCUMENTS

| 5,433,830 A | 7/1995 | Kawai et al. |
| 8,721,854 B2 | 5/2014 | Aoki et al. |

FOREIGN PATENT DOCUMENTS

| JP | 6-265522 A | 9/1994 |
| JP | 11-326266 A | 11/1999 |
| JP | 3855979 B2 | 9/2006 |

*Primary Examiner* — Eric Stapleton
(74) *Attorney, Agent, or Firm* — Global IP Counselors, LLP

(57) ABSTRACT

Provided is a method for recovering output of a gas sensor in shorter time. The method includes: determining a recovering temperature T1 and a recovering time Δτ1 based on a condition setting range where a high recovery rate is expected; and recovering the output based on T1 and Δτ1, wherein in the recovering, a duty ratio for a heater is instantly increased to value D1 higher than a value in a normal driving mode when the recovering starts, D1 is maintained up to T1, and PID control is performed by reducing the duty ratio to value D2 to maintain T1. After an elapse of Δτ1, the duty ratio is reduced to value D3. When the temperature of the element reaches a value 1 to 1.2 times as high as the temperature in the normal drive mode, the duty ratio is instantly changed to value D0 in the normal drive mode.

8 Claims, 10 Drawing Sheets

F I G. 1
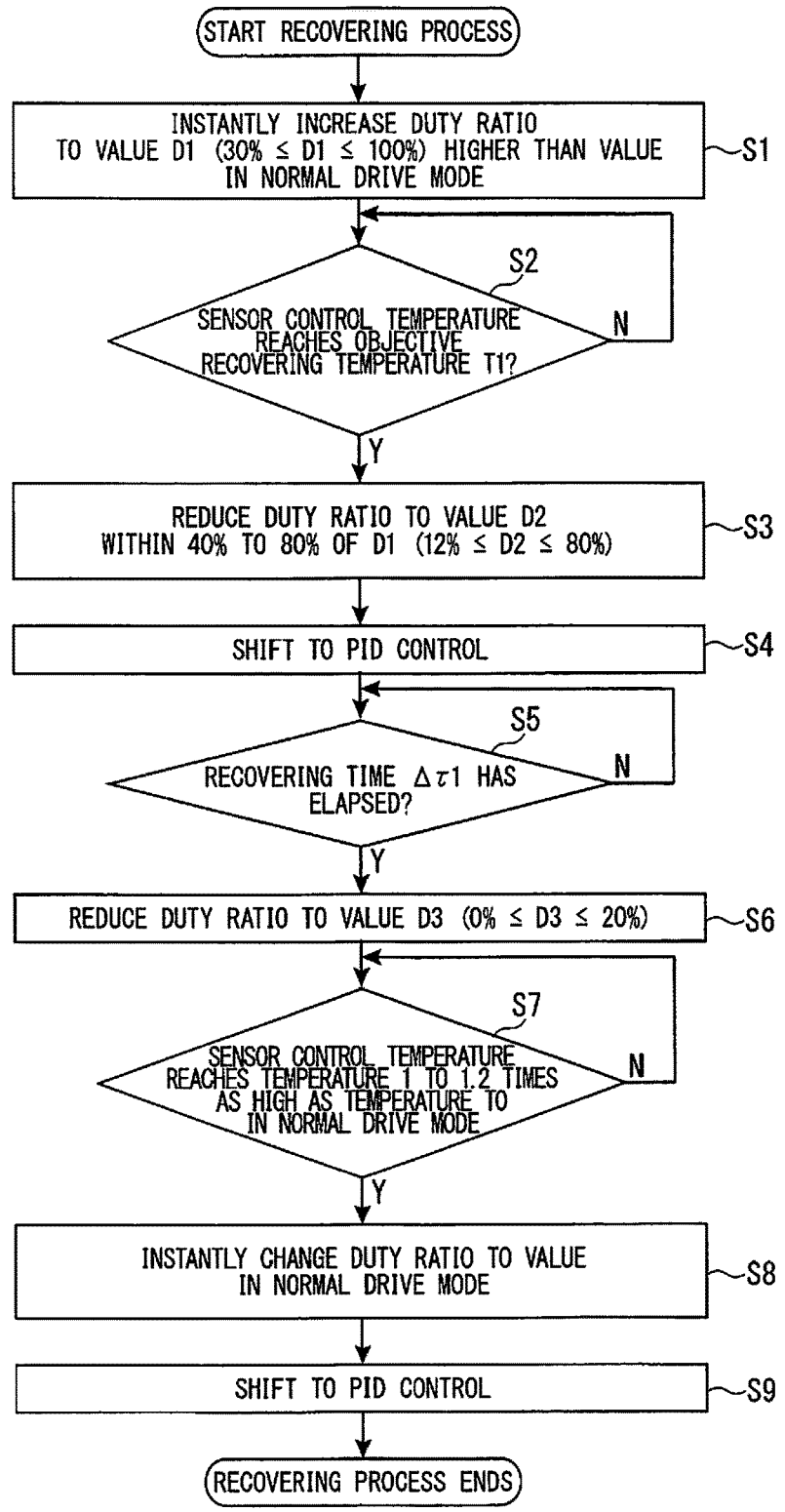

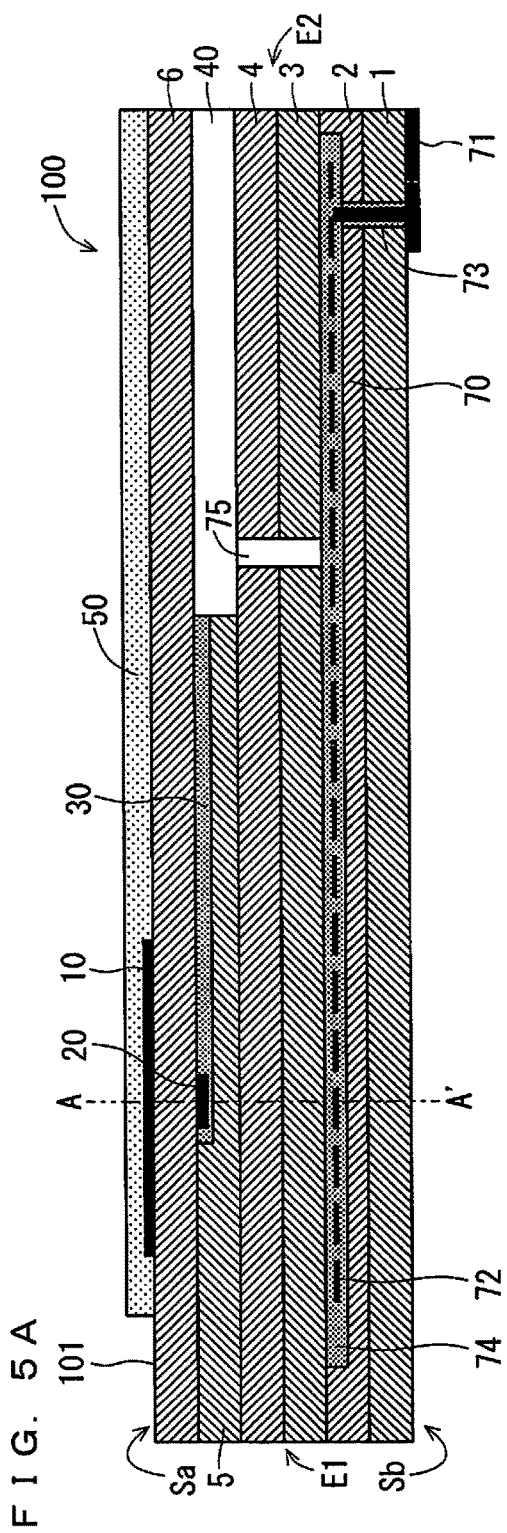
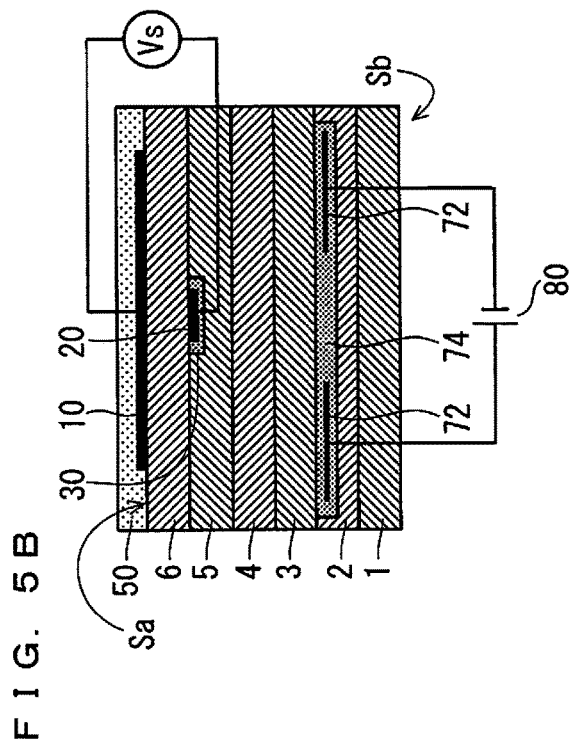
FIG. 5A
FIG. 5B

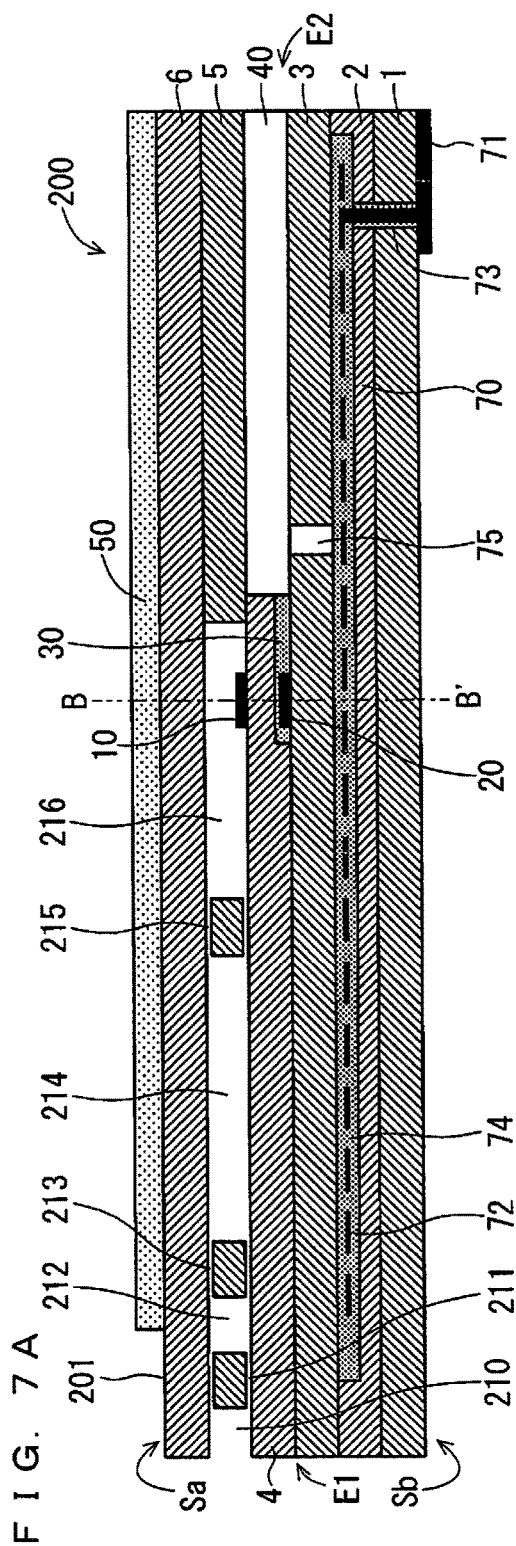
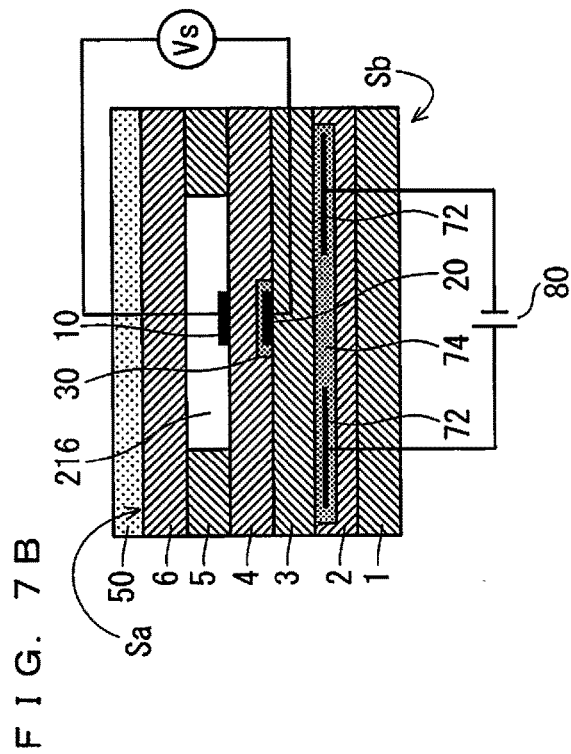
FIG. 7A
FIG. 7B

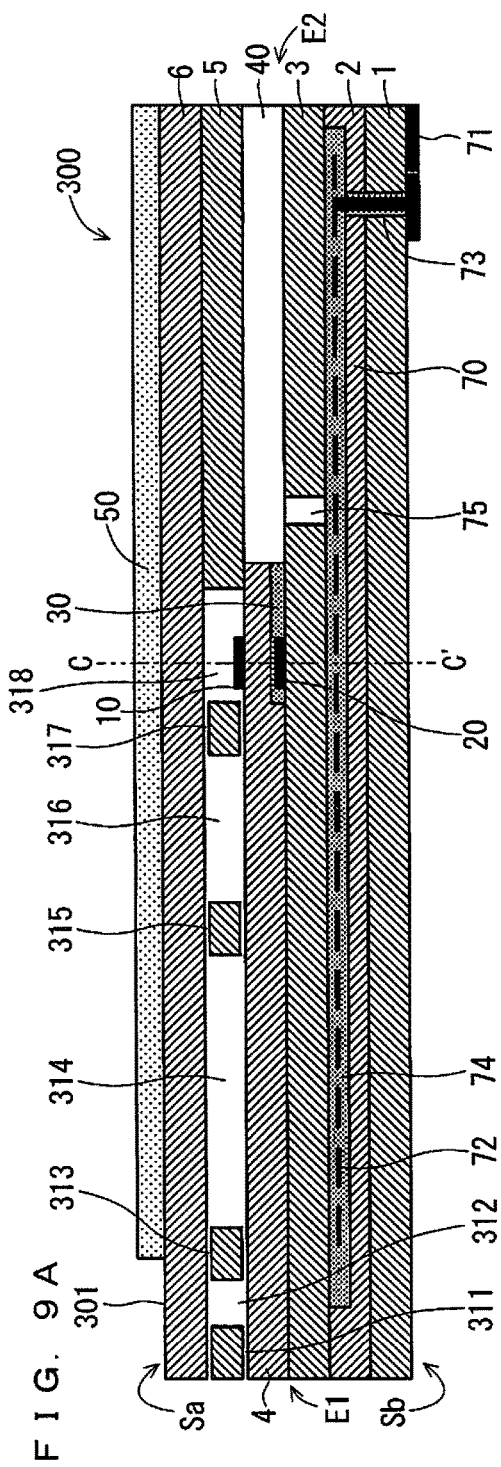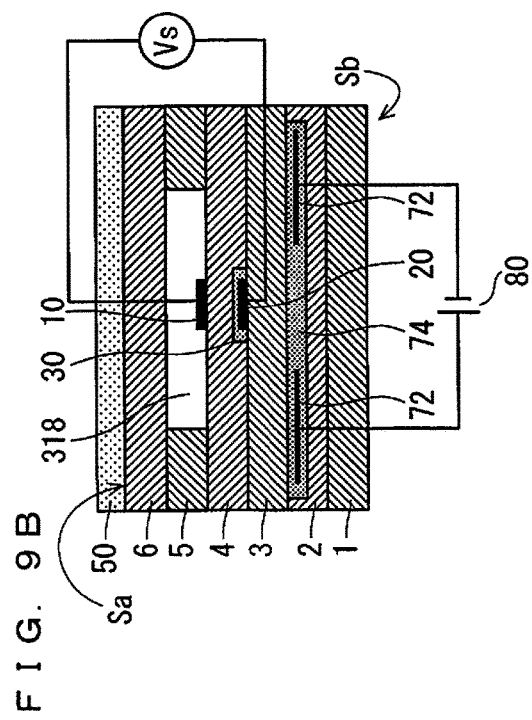

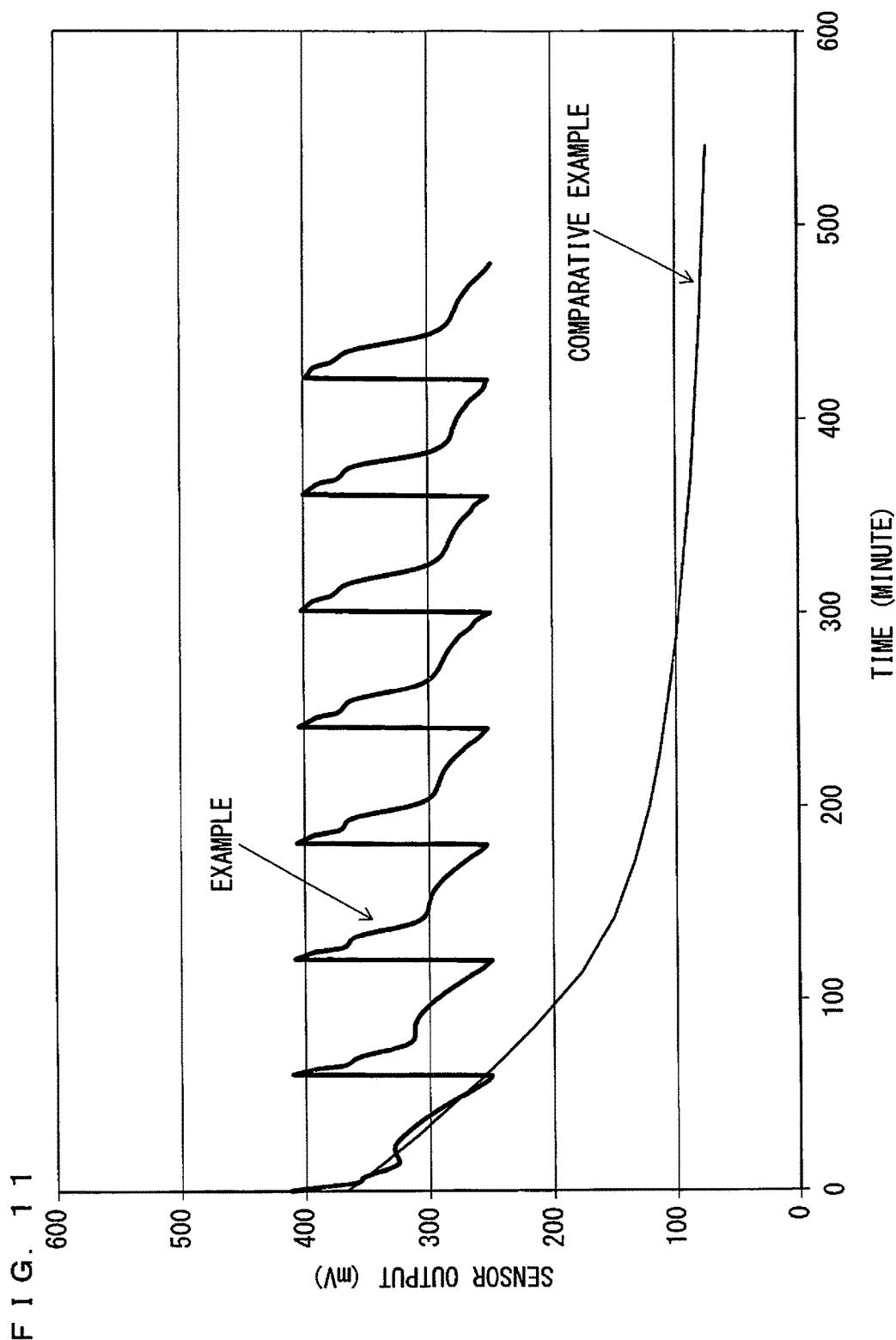

METHOD OF RECOVERING PROCESS FOR GAS SENSOR

BACKGROUND OF THE INVENTION

Field of the Invention

The present invention relates to a process for recovering output of a gas sensor, and in particular to a process for recovering the output by heating a sensor element mainly composed of a solid electrolyte.

Description of the Background Art

Gas sensors that sense a predetermined gas component of a measurement gas, such as an exhaust gas, to determine its concentration come in various types such as semiconductor gas sensor, catalytic combustion gas sensor, oxygen-concentration difference sensing gas sensor, limiting current gas sensor, and mixed-potential gas sensor. Among these gas sensors, sensor elements mainly made of ceramic that is a solid electrolyte such as zirconia and including an electrode mainly made of a noble metal are widely known.

It is also known, in the gas sensors including the sensor elements mainly made of ceramic such as zirconia, that a gas component or a poisoning substance in a measurement gas is adhered to the surface of the electrode and therefore the output value varies, during the long time use. When the output varies, a recovering process is executed to the sensor elements to achieve the original (initial) output value or to obtain an output value as close to the original output value as possible. Examples of the recovering process include an electrical process (see, for example, Japanese Unexamined Patent Application Publication No. H6-265522 and Japanese Patent No. 3855979) and a heating process (see, for example, Japanese Unexamined Patent Application Publication No. H11-326266).

The electrical process is a method for recovering output by alternately applying positive and negative potentials between electrodes that are paired through a solid electrolyte, so as to refine the electrodes or to desorb an adsorbed substance.

Meanwhile, the heating process is a method for recovering output with exposure of an adsorbed substance or a poisoning substance to a high temperature to desorb or burn (oxidize) the substance.

The recovering of output through the heating process generally requires a long processing time. Once executing the heating process to a sensor element, the gas sensor can neither be measured for concentration nor function until the temperature of the sensor element is recovered to the normal operating temperature. Thus, the processing time for the heating process is preferred to be as short as possible.

However, the heating time disclosed in Japanese Unexamined Patent Application Publication No. H11-326266 is as long as approximately 10 minutes. Although Japanese Unexamined Patent Application Publication No. H11-326266 describes heating a sensing element up to a preset temperature, it fails to disclose or suggest shortening the heating time by optimizing a temperature profile of the heating.

Furthermore, when a sensing electrode of a sensor element in a hydrocarbon gas sensor contains a larger amount of Au (gold) whose melting point is lower, exposure of the sensor element to a high temperature environment for a long time through the heating process may alter the properties of the sensing electrode and influence output of the gas sensor. Also in this respect, the heating time is preferably as short as possible when the sensor element of the hydrocarbon gas sensor is to be recovered.

SUMMARY OF THE INVENTION

The present invention relates to a process for recovering output of a gas sensor including a sensor element, and in particular to a process for recovering the output by heating a sensor element mainly composed of a solid electrolyte.

According to an aspect of the present invention, a method for recovering output of a gas sensor including a sensor element by heating the sensor element to a recovering temperature using a heater included in the sensor element, the recovering temperature being a second temperature higher than a first temperature that is a temperature of the sensor element in a normal drive mode, the method includes the following steps of: a) setting the recovering temperature and a recovering time, the recovering time being a time from start of increasing the first temperature up to the recovering temperature until end of maintaining the recovering temperature; and b) executing a recovering process based on the recovering temperature and the recovering time that are set in the step a), wherein in the step a), the recovering temperature and the recovering time are determined based on a condition setting range previously experimentally identified, the condition setting range being a range in which a recovery rate is expected to be higher than or equal to 95%, the recovery rate being a ratio of a difference in sensor output between immediately after and before the step b) to a difference between a sensor output when the gas sensor starts to be used and the sensor output immediately before the step b), and the step b) includes the following sub-steps of: b-1) heating the sensor element from the first temperature to the recovering temperature at the time when the step b) starts, by setting a duty ratio for the heater to a predetermined value D1 higher than a value in the normal drive mode when the sub-step b-1) starts, and maintaining the value D1 until the sensor element reaches the recovering temperature; b-2) maintaining the recovering temperature for a lapse of the recovering time after the sensor element reaches the recovering temperature through the sub-step b-1), by reducing the duty ratio to a value D2 which is not less than 40% of the value D1 and is not more than 80% of the value D1 and performing PID control whose control target value is the value D2; b-3) reducing the temperature of the sensor element by reducing the duty ratio to a value D3 lower than the value D2, at the time when the recovering time elapses through the sub-step b-2); and b-4) returning the sensor element to a control operation in the normal driving mode at the time when the temperature of the sensor element reaches a value 1 to 1.2 times as high as the first temperature through the sub-step b-3), by instantly changing the duty ratio to a value D0 in the normal drive mode and setting the value D0 to a control target value.

Since the recovering process according to the present invention achieves a higher recovery rate and a shorter processing time than those by the conventional method, a non-measurement time during which the gas sensor cannot measure the concentration of a measurement gas due to the recovering process is shortened more than by the conventional method.

Thus, the object of the present invention is to provide a method of a recovering process for a gas sensor thereby to recover output of the gas sensor for a shorter period of time than by the conventional method.

BRIEF DESCRIPTION OF THE DRAWINGS

FIG. 1 illustrates a procedure of a recovering process for a gas sensor;

FIGS. 5A and 5B illustrate a schematic structure of a gas sensor 100;

FIGS. 7A and 7B illustrate a schematic structure of a gas sensor 200;

FIGS. 9A and 9B illustrate a schematic structure of a gas sensor 300;

FIG. 11 illustrates a temporal change in sensor output of gas sensors according to Example and the comparative example.

DESCRIPTION OF THE PREFERRED EMBODIMENTS

[Recovering Process for Gas Sensor and its Procedure]

Figure 2:
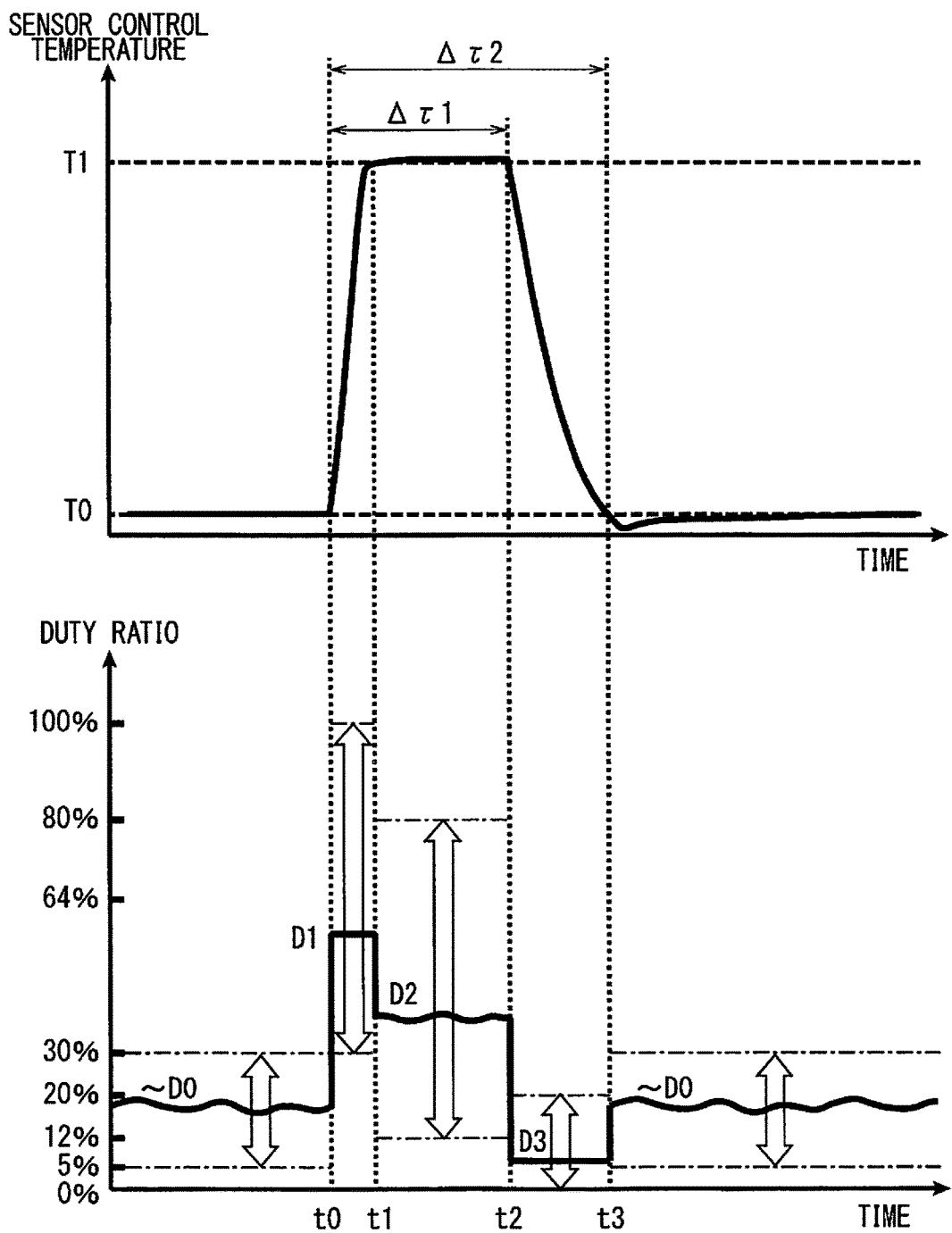
FIG. 2 illustrates a temporal change in sensor control temperature and duty ratio of a heater in a recovering process.
Figure 3:
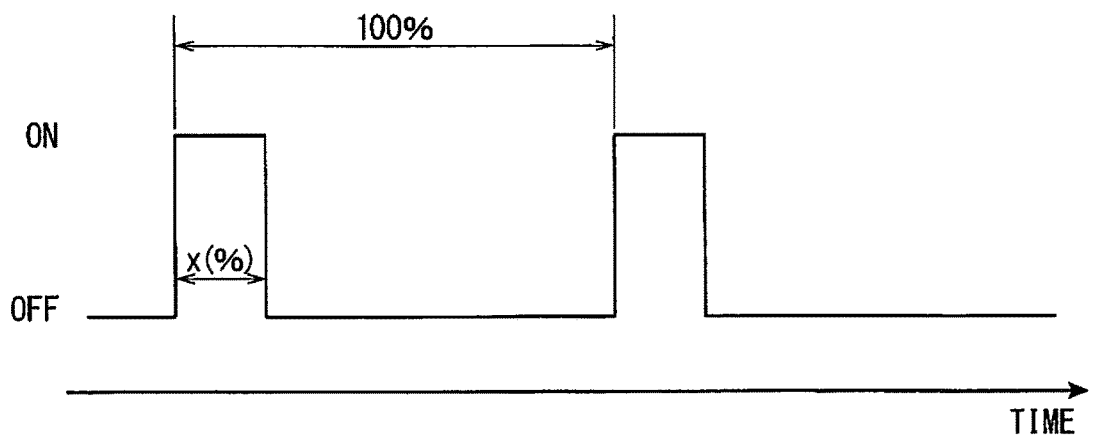
FIG. 3 is an explanatory diagram of a duty ratio.

FIG. 1 illustrates a procedure of a recovering process for a gas sensor according to this embodiment. FIG. 2 illustrates a temporal change in sensor control temperature and duty ratio of a heater in the recovering process. FIG. 3 is an explanatory diagram of the duty ratio.

In summary, the recovering process according to this embodiment is a heating process to a gas sensor so that output of the gas sensor (sensor output) that decreases over time is equal to the initial value or as close to it as possible.

In this embodiment, the gas sensor which preferably determines the concentration of an unburned hydrocarbon gas in a measurement gas is subjected to the recovering process, where the measurement gas is, for example, an exhaust gas present in an exhaust pipe of an engine aboard a diesel vehicle. In the specification, examples of the unburned hydrocarbon gas include carbon monoxide (CO) and hydrogen in addition to typical hydrocarbon gases (gases classified as hydrocarbon in terms of chemical formula) such as $C_2H_4$, $C_3H_6$, and n-C8.

Specifically, the gas sensor to be subjected to the recovering process in this embodiment includes a sensor element mainly made of zirconia ($ZrO_2$) that is an oxygen-ion conductive solid electrolyte, and obtains, as a sensor output in the sensor element, a potential difference between a sensing electrode in contact with a measurement gas atmosphere and a reference electrode in contact with an atmosphere in which the concentration of oxygen is constant. Based on the sensor output, the concentration of a hydrocarbon gas component in the measurement gas can be obtained.

Furthermore, the sensor element includes a heater that heats the whole sensor element. The heater heats the sensor element with energization from a heater power source outside the sensor element to the heater, not only when the gas sensor is actually used (in a normal driving mode) but also when the recovering process is executed. A temperature of the sensor element to be controlled by heating of the heater will be hereinafter referred to as a "sensor control temperature". The sensor control temperature can be actually measured by converting a resistance value of the heater in energization, and is always monitored by monitoring the resistance value.

The energization to the heater is performed by cyclically repeatedly switching between ON and OFF as illustrated in FIG. 3. The duty ratio (unit:%) is a rate of one period in which the heater is turned ON (a rate of a time during which an electric current is actually applied) relative to one cycle of the ON and OFF. In the following, the duty ratio will be expressed by its value when an applied voltage to the heater is 14 V.

In the normal driving mode where the recovering process is not executed (that is, when the sensor output can be obtained), the heater is under PID control in which the sensor control temperature is maintained as a value T0 in the gas sensor (see FIG. 2). Here, the control target value of the duty ratio is assumed as D0, where 5%≤D0≤30%.

Now at a time t=t0, the recovering process starts (see FIG. 2). To start the recovering process, first, the duty ratio is instantly increased to a predetermined value D1 higher than a value in the normal drive mode (approximately D0) (Step S1), where 30%≤D1≤100%.

With increase in the duty ratio, the sensor element is heated, and the sensor control temperature increases. Until the sensor control temperature reaches a predetermined recovering temperature T1 (No at Step S2), the duty ratio is maintained as the value D1.

When the sensor control temperature reaches the recovering temperature T1 at a certain time t=t1 (Yes at Step S2), the duty ratio is reduced from the value D1 (Step S3) to maintain the recovering temperature T1, and the PID control whose control target value is a value D2 which is not less than 40% and not more than 80% of D1 (that is, 12%≤D2≤80%) (Step S4) is performed.

Maintaining the recovering temperature T1 is continued up to a time t=t2=t0+Δτ1, at which an elapsed time from the time t=t0 is equal to a predetermined recovering time Δτ1 (No at Step S5). Maintaining the sensor element at the recovering temperature T1 allows an adsorbed substance or a poisoning substance adhered to, for example, the sensing electrode of the sensor element to desorb.

The recovering temperature T1 and the recovering time Δτ1 are determined based on a condition range (high-recovery rate range) of recovering temperatures and recovering times which were previously experimentally identified and at which a high recovery rate is expected. The recovery rate is a ratio of a difference in sensor output between immediately after and before the recovering process, to a difference between a sensor output when the gas sensor starts to be used and the sensor output immediately before the recovering process. How to set the recovering temperature T1 and the recovering time Δτ1 will be described later in detail.

At the time t=t2 at which the recovering time Δτ1 has elapsed (Yes at Step S5), the duty ratio is reduced to a value D3 lower than the value D2 so that the sensor control temperature is to decrease from the recovering temperature T1 to the temperature T0 in the normal drive mode (Step S6), where 0%≤D3≤20%.

Until the sensor control temperature reaches a value 1 to 1.2 times as high as the temperature T0 (No at Step S7), the duty ratio is maintained as the value D3.

When the sensor control temperature reaches the value 1 to 1.2 times as high as the temperature T0 at a certain time t=t3 (Yes at Step S7), the duty ratio is instantly changed to the value D0 in the normal drive mode (Step S8), and the PID control whose control target value is the value D0 (Step S9) is performed. In other words, the sensor element is returned to a control operation in the normal drive mode.

The procedure of the recovering process in this embodiment is hereinbefore described.

[Setting Recovering Temperature and Recovering Time]

As illustrated in FIG. 2, the recovering process according to this embodiment has a non-measurement time ($\Delta\tau 2 = t3 - t0$) between $t=t0$ and $t=3$ at which no sensor output is obtained. Since gas sensors are generally required to be continuously in use in order to measure the concentration of a measurement gas in real time, the non-measurement time is preferably as short as possible. Meanwhile, the recovering process is executed to sufficiently produce the advantage with one process, that is, to achieve a higher recovery rate. Furthermore, it is necessary to consider that extremely increasing the recovering temperature T1 may melt and degrade the electrodes included in the sensor element. Normally, the recovering temperature T1 may be set to a value approximately 200° C. to 500° C. higher than the temperature T0 in the normal drive mode.

In this embodiment, a condition range (high-recovery rate range) of recovering temperatures and recovering times at which a high recovery rate is expected is previously experimentally identified, and the recovering temperature T1 and the recovering time $\Delta\tau 1$ for the recovering process are determined based on the high-recovery rate range.

Specifically, a plurality of unused gas sensors are prepared. After measurement of initial sensor outputs (assuming the output values as y0), a degrading process for intentionally reducing the sensor outputs, and measurement of the sensor outputs after the degrading process (assuming the output values as y1) to all of the gas sensors under the common conditions, the recovering process is executed to each of the gas sensors according to the procedure illustrated in FIG. 1 under a different process condition (a different combination of the recovering temperature and the recovering time). Furthermore, measurement of the sensor outputs after the recovering process to all of the gas sensors is performed under the common conditions (assuming the output values as y2), and a recovery rate r (%) is calculated for each of the gas sensors with the following Equation (1):

$$r(\%) = \{(y2-y1)/(y0-y1)\} \times 100 \quad (1).$$

Here, the sensor outputs are measured using, as a measurement gas, a reference gas having a composition similar to that of the measurement gas in actual use. Furthermore, the degrading process is performed by exposing, for a predetermined time, each of the gas sensors to a gas atmosphere in which the concentration of an unburned hydrocarbon gas is sufficiently higher than that of the reference gas.

Then, the high-recovery rate range is defined as a range of recovering temperatures and recovering times in which the recovery rate r is higher than or equal to 95%. When the recovery rate r is higher than or equal to 95%, it could be regarded that the sensor output has been sufficiently recovered in view of the measurement accuracy of the gas sensor. Furthermore, since the conditions for the degrading process are defined to reduce the sensor output to a degree at least higher than or equal to a degree of reduction in the actual sensor output of the gas sensor, when the recovering temperature T1 and the recovering time $\Delta\tau 1$ are determined based on the high-recovery rate range, a higher recovery rate of 95% or higher can be expected for the sensor output of the gas sensor to which the recovering process is actually executed.

Finally, a range in which the temperature does not exceed the melting point of the electrodes and the recovering time is as short as possible is determined as a condition setting range RE from the identified high-recovery rate range, and then, the recovering temperature T1 and the recovering time $\Delta\tau 1$ for the recovering process are determined based on the condition setting range RE.

Figure 4:
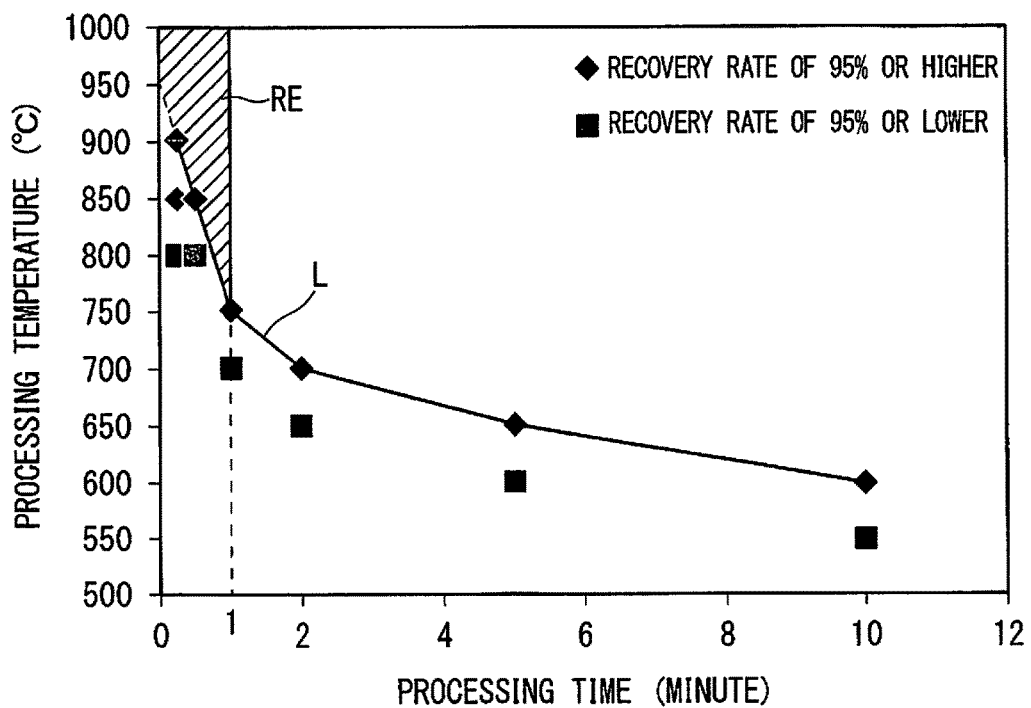
FIG. 4 illustrates a condition setting range RE of, for example, a mixed-potential gas sensor.

FIG. 4 illustrates the condition setting range RE of, for example, a mixed-potential gas sensor (see FIGS. 5A and 5B) having a temperature T0=500° C. in the normal drive mode, and including a sensing electrode 10 containing Au (gold) whose melting point is 1064° C. on an outer surface of the sensor element. When the result illustrated in FIG. 4 is obtained, the reference gas consists of $C_2H_4$=300 ppm, $O_2$=10%, $H_2O$=5%, and $N_2$=a residue, the gas atmosphere in the degrading process consists of $C_2H_4$=2000 ppm, $O_2$=10%, and $N_2$=a residue, and the processing time for the degrading process is 15 minutes.

In FIG. 4, the values representing the recovery rates r that are higher than or equal to and the closest to 95% are plotted by rhombuses (♦), and the values representing the recovery rates r that are less than and the closest to 95% are plotted by rectangles (■).

In FIG. 4, the high-recovery rate range is a range in which recovering temperatures are higher than those of a curve L obtained by connecting data points of the rhombuses. The curve L tends to have a higher recovering temperature as the recovering time is shorter, which indicates that the recovering temperature T1 needs to be increased to achieve a higher recovery rate r with a shorter recovering time $\Delta\tau 1$.

Furthermore, the condition setting range RE is set to a range in which the temperature is lower than or equal to 1000° C. that is lower than the melting point of Au and the recovering time is shorter than or equal to 1 minute. When the recovering process is executed under the procedure illustrated in FIG. 1 with the recovering temperature T1 and the recovering time $\Delta\tau 1$ determined from the condition setting range RE, it is expected that the gas sensor is recovered at the high recovery rate r that is higher than or equal to 95% with a shorter recovering time and a shorter non-measurement time.

FIG. 4 illustrates the curve L indicating the high-recovery rate range and the condition setting range RE of the gas sensor including a sensing electrode at an outer surface of the sensor element. The condition setting range RE illustrated in FIG. 4 is also applicable to the gas sensor having a different structure, as long as it is identical to the gas sensor exemplified in FIG. 4 in composition of the electrode, constituent of the sensor element, and type of the measurement gas. The requirements on the recovering temperature have only to be satisfied at least in the vicinity of the sensing electrode, and the temperature, for example, in the vicinity of the heater or the entire ceramic portion may exceed an upper temperature range of the condition setting range RE, within the confines where the characteristics of the sensor element is not influenced.

As described above, according to this embodiment, before the recovering process for recovering the sensor output of the gas sensor is executed by the heating process to the sensor element, the recovering temperature and the recovering time are determined based on a condition range previously and experimentally identified in which the recovery rate higher than or equal to 95% is expected, so that the recovering temperature does not exceed the melting point of the electrodes and that the recovering time is shortened as much as possible. In the actual recovering process, the sensor element is heated from the temperature in the normal drive mode to the recovering temperature in a manner that the duty ratio for the heater included in the sensor element is instantly increased to the predetermined value D1 higher than the value in the normal drive mode, and the value D1 is maintained until the temperature of the sensor element reaches the recovering temperature. After the temperature reaches the recovering temperature, the duty ratio is reduced to the value D2 which is not less than 40% of D1 and not more than 80% of D1. Until the recovering time elapses, the PID control whose control target value is the value D2 is performed to maintain the recovering temperature. At the time when the recovering time elapses, the duty ratio is reduced to the value D3 lower than the value D2 to reduce the temperature of the sensor element. When the temperature of the sensor element reaches a value 1 to 1.2 times as high as the temperature in the normal drive mode, the duty ratio is instantly changed to the value D0 in the normal drive mode, so that the sensor element is returned to a control operation in the normal drive mode using the value D0 as the control target value.

Since a higher recovery rate and a shorter processing time than those by the conventional method are achieved by the recovering process with the conditions described above, a non-measurement time during which the gas sensor cannot measure the concentration of a measurement gas due to the recovering process is shortened more than by the conventional method.

The continuous use of the recovery-processed gas sensor reduces the sensor output again. If so, the recovering process may be performed again. Specifically, the recovering process can produce the advantages even with repetition thereof. In other words, the recovering process with appropriate timing can prolong the life of the gas sensor.

EXAMPLES

Three types of gas sensors differing in structure of sensor elements were recovering as examples of the embodiment.

Example 1

Outline of Sensor Element

FIGS. 5A and 5B illustrate a schematic structure of a gas sensor 100 that was subjected to the recovering process according to Example 1. FIG. 5A is a vertical cross-sectional view of a sensor element 101 being a main component of the gas sensor 100, which is taken along the longitudinal direction of the sensor element 101 (hereinafter referred to as a "element longitudinal direction"). FIG. 5B is a view including a cross-section of the sensor element 101 vertical to the element longitudinal direction, which is taken along a line A-A" of FIG. 5A.

The gas sensor 100 is a mixed-potential gas sensor that determines the concentration of a gas component to be measured in a measurement gas, using a potential difference between the sensing electrode 10 disposed on the surface of the sensor element 101 mainly composed of ceramic being an oxygen-ion conductive solid electrolyte such as zirconia ($ZrO_2$) and a reference electrode 20 disposed inside the sensor element 101, due to a difference in the concentration of the gas component in the vicinity of the sensing electrode 10 and the reference electrode 20 on the basis of the principle of mixed potential.

Furthermore, the sensor element 101 mainly includes a reference gas introduction layer 30, a reference gas introduction space 40, and a surface protective layer 50 in addition to the sensing electrode 10 and the reference electrode 20.

The sensor element 101 has a structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte are laminated in the stated order from the bottom side of FIGS. 5A and 5B. The sensor element 101 additionally includes other components mainly between those layers or on an outer peripheral surface of the element. The solid electrolytes constituting those six layers are fully airtight. The sensor element 101 is manufactured by, for example, laminating ceramic green sheets corresponding to the individual layers, which have been subjected to a predetermined process and printing of a circuit pattern, and further, by integrating the laminated layers through firing.

The sensing electrode 10 is an electrode for sensing a measurement gas. The sensing electrode 10 is formed as a porous cermet electrode made of Pt containing a predetermined ratio of Au, namely, Pt—Au alloy and zirconia. The sensing electrode 10 is provided in a substantially rectangular shape in plan view at a position close to the distal end E1, being one end in the longitudinal direction of the sensor element 101, on a front surface Sa of the sensor element 101 (the top surface of the sixth solid electrolyte layer 6 in FIGS. 5A and 5B). The gas sensor 100 is placed such that, in its use, a portion where at least the sensing electrode 10 is provided is exposed to a measurement gas.

Specifically, the sensing electrode 10 has an Au abundance ratio of 0.7 by containing 10 wt % of Au in the Pt—Au alloy included in the sensing electrode 10. Accordingly, the catalytic activation of the sensing electrode 10 against an unburned hydrocarbon gas is disabled. In other words, the decomposition reaction of an unburned hydrocarbon gas in the sensing electrode 10 is suppressed. In the gas sensor 100, accordingly, the potential of the sensing electrode 10 selectively varies with respect to (has correlation with) the unburned hydrocarbon gas, in accordance with its concentration. In other words, the sensing electrode 10 is provided so as to have high dependence of potential on concentration for an unburned hydrocarbon gas while having low dependence of potential on concentration for components of other measurement gas.

In this specification, the Au abundance ratio means an area ratio of a portion covered with Au to a portion at which Pt is exposed in the surface of noble metal particles forming the sensing electrode 10. The Au abundance ratio is 1 when the area of the portion at which Pt is exposed is equal to the area of the portion covered with Au. In this specification, an Au abundance ratio is calculated from a peak intensity of a peak detected for Au and Pt, obtained by X-ray photoelectron spectroscopy (XPS) using a relative sensitivity coefficient method.

For an Au abundance ratio of 0.3 or more, in the sensing electrode 10, Au is concentrated on the surface of noble metal particles forming the sensing electrode 10. In more detail, an Au-rich Pt—Au alloy is formed near the surface of Pt-rich Pt—Au alloy particles. When such a state is achieved, the catalytic activation in the sensing electrode 10 is preferably disabled, increasing the dependence of the potential of the sensing electrode 10 on the concentration of an unburned hydrocarbon gas.

Furthermore, the volume ratio between noble metal components and zirconia in the sensing electrode 10 may be about from 5:5 to 8:2, and is 6:4 according to Example 1.

For the gas sensor 100 to preferably exhibit their functions, the porosity of the sensing electrode 10 is preferably 10% or more and 30% or less, and the thickness of the sensing electrode 10 is preferably 5 μm or more. In particular, the porosity is more preferably 15% or more and 25% or less, and the thickness is more preferably 25 μm or more and 35 μm or less. According to Example 1, the porosity of the sensing electrode 10 is 20%, and the thickness of the sensing electrode 10 is 25 μm.

The reference electrode 20 is an electrode substantially rectangular in plan view, which is provided inside the sensor element 101 and serves a reference when the concentration of a measurement gas is determined. Specifically, the reference electrode 20 is provided to be covered by the reference gas introduction layer 30 between the fifth solid electrolyte layer 5 and the sixth solid electrolyte layer 6. The reference electrode 20 is formed as a porous cermet electrode made of Pt and zirconia.

The reference gas introduction layer 30 is a layer made of porous alumina, which is provided to cover the reference electrode 20 between the fifth solid electrolyte layer 5 and the sixth solid electrolyte layer 6 and to extend in the element longitudinal direction. The reference gas introduction space 40 is an internal space provided in such a manner that part of the fifth solid electrolyte layer 5 is in communication with the outside on the base end E2 side of the sensor element 101. Air (oxygen), serving as a reference gas when the concentration of an unburned hydrocarbon gas is determined, is externally introduced into the reference gas introduction space 40.

The reference gas introduction space 40 and the reference gas introduction layer 30 are in communication with each other, and accordingly, in the use of the gas sensor 100, the surroundings of the reference electrode 20 are always filled with air (oxygen) through the reference gas introduction space 40 and the reference gas introduction layer 30. During the use of the gas sensor 100, therefore, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even if the sensing electrode 10 is exposed to the measurement gas.

The surface protective layer 50 is provided so as to cover at least the sensing electrode 10 on the front surface Sa of the sensor element 101. The surface protective layer 50 is a porous layer made of alumina, and is provided as an electrode protective layer that prevents the degradation of the sensing electrode 10 due to continuous exposure to a measurement gas during the use of the gas sensor 100.

As shown in FIG. 5B, in the gas sensor 100, a potentiometer that is not illustrated can measure a potential difference Vs between the sensing electrode 10 and the reference electrode 20, and the potential difference Vs is used as a sensor output.

Furthermore, the sensor element 101 further includes a heater part 70. The heater part 70 includes a heater electrode 71, a heater 72, a through-hole 73, a heater insulating layer 74, and a pressure diffusion hole 75. The heater part 70 heats the sensor element 101 (specifically, the solid electrolyte constituting the sensor element 101), and maintains a temperature of the sensor element 101 in the normal drive mode and in the recovering process.

In the heater part 70, the heater 72 that is an electric resistor provided inside the sensor element 101 is electrically connected with a heater power source 80 outside the sensor element 101 as schematically illustrated in FIG. 5B. Specifically, as illustrated in FIG. 5A, the heater 72 is connected through the through-hole 73 with the heater electrode 71 formed to come into contact with the rear surface Sb of the sensor element 101 (the lower surface of the first solid electrolyte layer 1 in FIG. 5A). The heater power source 80 applies voltage to the heater 72 through the heater electrode 71.

The heater insulating layer 74 is an insulating layer made of an insulator such as alumina on the upper and lower surfaces of the heater 72. The heater insulating layer 74 is formed for the electrical insulation between the second solid electrolyte layer 2 and the heater 72 and for the electrical insulation between the third solid electrolyte layer 3 and the heater 72.

The pressure diffusion hole 75 is a part provided to penetrate the third solid electrolyte layer 3 and to be in communication with the reference gas introduction space 40, which is formed to mitigate an internal pressure rise associated with a temperature rise in the heater insulating layer 74.

To determine the concentration of an unburned hydrocarbon gas in a measurement gas using the gas sensor 100 having such a structure, as described above, air (oxygen) is supplied to the reference gas introduction space 40, with the sensor element 101 in only a predetermined range, which starts from the distal end E1 and includes at least the sensing electrode 10, being disposed in a space in which a measurement gas is present, and with the sensor element 101 on the base end E2 side being disposed apart from the space. The sensor element 101 is heated by the heater 72 to an appropriate temperature from 400° C. to 800° C., preferably from 500° C. to 700° C., and more preferably from 500° C. to 600° C.

The concentration of an unburned hydrocarbon gas in a measurement gas can be determined almost in real time, because the potential difference Vs between the sensing electrode 10 exposed to the measurement gas and the reference electrode 20 disposed in the air is associated with values representing the composition of the measurement gas present around the sensing electrode 10.

Although the gas sensor 100 includes the surface protective layer 50 covering the sensing electrode 10, a gas component or a poisoning substance in a measurement gas is adhered to the sensing electrode 10 by the continuous use of the gas sensor 100. Thus, the recovering process needs to be performed with appropriate timing to prevent the degradation of the sensor output.

[Recovering Process]

The gas sensor 100 with the structure above was subjected to the recovering process after its use. The gas sensor 100 was used under the following conditions in the normal drive mode, where the initial sensor output y0 was 275 mV and the sensor output y1 before the recovering process was 200 mV:

T0=500° C.; and

D0=10%.

Prior to execution of the recovering process, the unused gas sensor 100 was prepared to set the recovering temperature T1 and the recovering time $\Delta\tau1$, and the condition setting range RE was determined based on the conditions illustrated in FIG. 4. In other words, the result illustrated in FIG. 4 is of the gas sensor 100 according to Example 1. Then, the recovering temperature T1=850° C. and the recovering time $\Delta\tau1$=30 seconds were determined based on the condition setting range RE. Besides, condition values of the duty ratio were defined as follows:

D1=65%;
D2=35%; and
D3=1%.

The recovering process was performed under the above conditions according to the procedure illustrated in FIG. 1.

Figure 6:
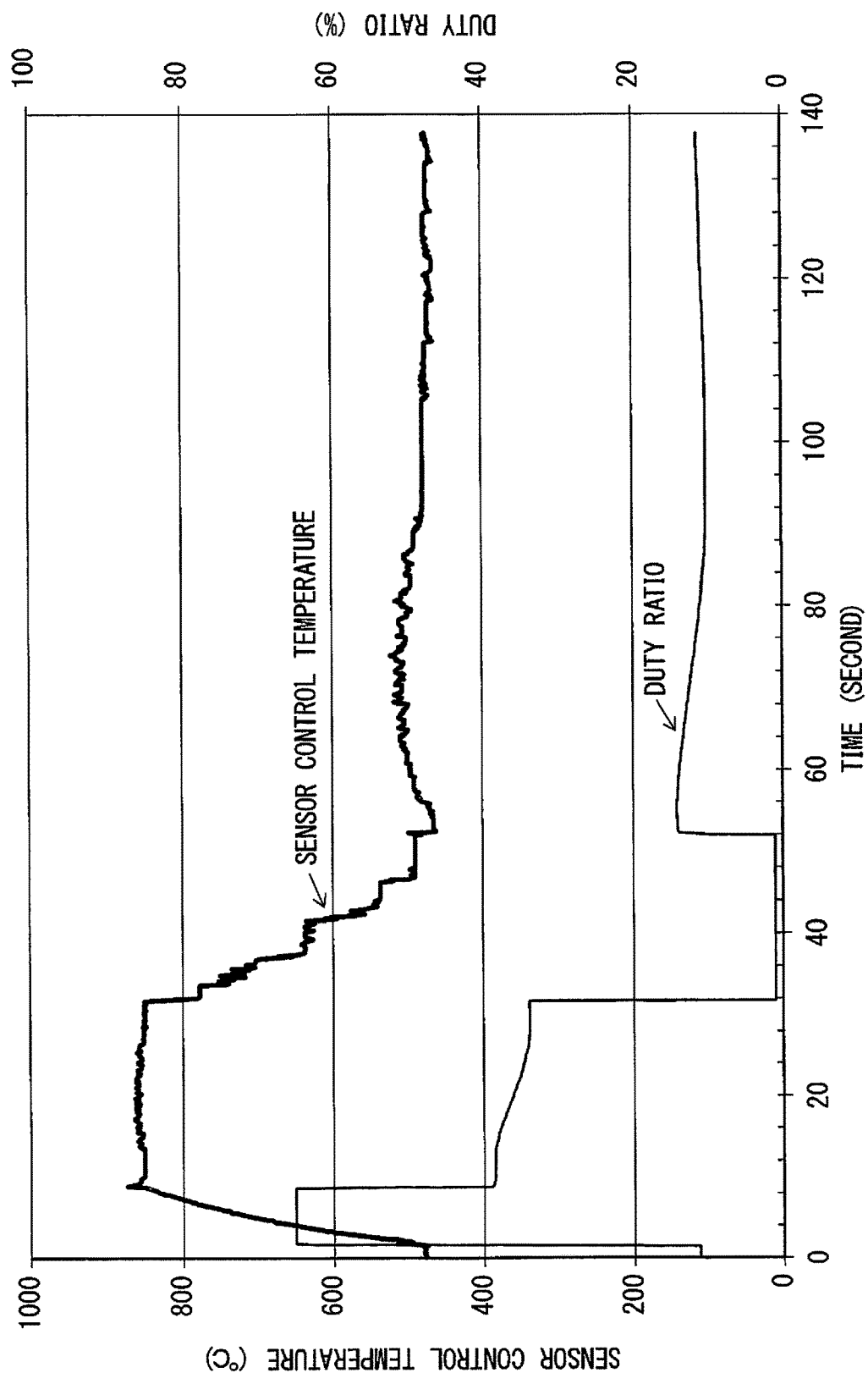
FIG. 6 illustrates a temporal change in sensor control temperature and duty ratio of the gas sensor 100 in the recovering process.

FIG. 6 illustrates a temporal change in sensor control temperature and duty ratio of the gas sensor 100 in the recovering process. A non-measurement time $\Delta\tau2$ determined from the change in duty ratio illustrated in FIG. 6 was approximately 50 seconds. Since the sensor output y2 after the recovering process was 272.8 mV, the actual recovery rate r in the recovering process was 97% according to Equation (1).

Specifically, a higher recovery rate of the gas sensor 100 was obtained with a shorter recovering time and a shorter non-measurement time according to Example 1.

Example 2

Outline of Sensor Element

FIGS. 7A and 7B illustrate a schematic structure of a gas sensor 200 that was subjected to the recovering process according to Example 2. FIG. 7A is a vertical cross-sectional view of a sensor element 201 being a main component of the gas sensor 200 along a longitudinal direction of the sensor element 201 (hereinafter referred to as a "element longitudinal direction"). FIG. 7B is a view including a cross-section of the sensor element 201 vertical to the element longitudinal direction, which is taken along a line B-B' of FIG. 7A.

As the gas sensor 100 according to Example 1, the gas sensor 200 determines the concentration of a gas component to be measured in a measurement gas, using a potential difference between the sensing electrode 10 and the reference electrode 20 due to a difference in the concentration of the gas component in the vicinity of the sensing electrode 10 and the reference electrode 20 on the basis of the principle of mixed potential. Thus, the constituent elements of the gas sensor 200 identical to those of the gas sensor 100 are denoted by the same reference numerals, and the detailed description thereof will be omitted.

The gas sensors 100 and 200 differ in that the sensing electrode 10 of the gas sensor 100 is placed on the upper surface of the sensor element 101, whereas the sensing electrode 10 is placed inside the sensor element 201 of the gas sensor 200.

Specifically, a gas inlet 210, a first diffusion control part 211, a buffer space 212, a second diffusion control part 213, a first internal space 214, a third diffusion control part 215, and a second internal space 216 are adjacently formed so as to be in communication with one another in the element longitudinal direction in stated order, between the lower surface of the sixth solid electrolyte layer 6 and the upper surface of the fourth solid electrolyte layer 4 at the distal end E1 of the sensor element 201. The sensor element 201 is a two-chamber serial type sensor element. The part extending from the gas inlet 210 to the second internal space 216 is also referred to as a gas distribution part.

The gas inlet 210, the buffer space 212, the first internal space 214, and the second internal space 216 are interior spaces provided by hollowing out the fifth solid electrolyte layer 5. The buffer space 212, the first internal space 214, and the second internal space 216 are each provided, with its upper portion defined by the lower surface of the sixth solid electrolyte layer 6, its lower portion defined by the upper surface of the fourth solid electrolyte layer 4, and its side portion defined by the side surface of the fifth solid electrolyte layer 5.

Meanwhile, each of the first diffusion control part 211, the second diffusion control part 213, and the third diffusion control part 215 is provided as two horizontally long slits which are openings longitudinally extending perpendicular to the drawing of FIG. 7A.

Furthermore, the sensing electrode 10 in the sensor element 201 is provided in the second internal space 216 (facing the second internal space 216). The reference electrode 20 is disposed to be covered by the reference gas introduction layer 30 between the third solid electrolyte layer 3 and the fourth solid electrolyte layer 4.

The reference gas introduction layer 30 is provided to cover the reference electrode 20 between the third solid electrolyte layer 3 and the fourth solid electrolyte layer 4 and to extend in a longitudinal direction of the sensor element 201. The reference gas introduction space 40 is provided in such a manner that part of the fourth solid electrolyte layer 4 is in communication with the outside on the base end E2 side of the sensor element 201.

In the sensor element 201, a measurement gas is introduced from the outside space to inside through the gas inlet 210 that is an opening to the outside. The measurement gas is given a predetermined diffusion resistance through the first diffusion control part 211, the second diffusion control part 213, and the third diffusion control part 215, and reaches the vicinity of the sensing electrode 10 in the second internal space 216 after an electrochemical oxygen pump cell whose illustration is omitted adjusts the concentration of oxygen in the first internal space 214 and the second internal space 216 so as not to influence the sensing of an unburned hydrocarbon gas.

In the gas sensor 200 having the structure above, the concentration of an unburned hydrocarbon gas in a measurement gas can be determined almost in real time by heating the sensor element 201 to an appropriate temperature using the heater 72 and measuring the potential difference Vs between the sensing electrode 10 and the reference electrode 20. By the continuous use of the gas sensor 200, a gas component or a poisoning substance in a measurement gas is adhered to the sensing electrode 10. Accordingly, the recovering process needs to be performed with appropriate timing to prevent the degradation of the sensor output.

[Recovering Process]

The gas sensor 200 with the structure above was subjected to the recovering process after its use. The gas sensor 200 was used under the following conditions in the normal drive mode, where the initial sensor output y0 was 240 mV and the sensor output y1 before the recovering process was 185 mV;

T0=650° C. (here, the temperature in the vicinity of the sensing electrode 10 was 500° C.); and

D0=20%.

Prior to execution of the recovering process, the recovering temperature T1=1000° C. and the recovering time $\Delta\tau1$=30 seconds were determined based on the condition setting range RE in FIG. 4. It was previously confirmed that the temperature in the vicinity of the sensing electrode 10 when T1=1000° C. approximately reached 850° C. Besides, condition values of the duty ratio were defined as follows:

D1=75%;
D2=50%; and
D3=1%.

The recovering process was performed under the above conditions according to the procedure illustrated in FIG. 1.

Figure 8:
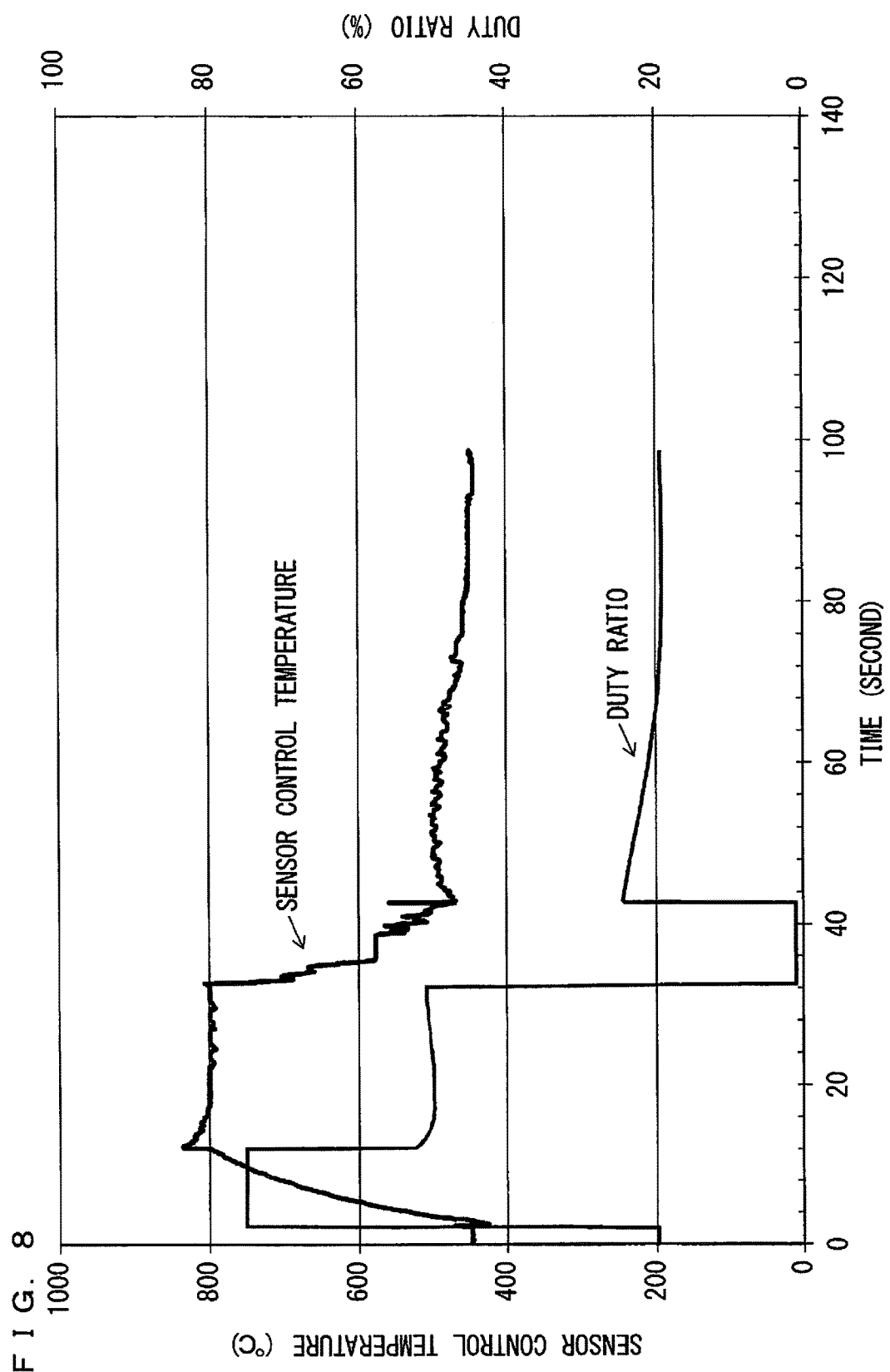
FIG. 8 illustrates a temporal change in sensor control temperature and duty ratio of the gas sensor 200 in the recovering process.

FIG. 8 illustrates a temporal change in sensor control temperature and duty ratio of the gas sensor 200 in the recovering process. The non-measurement time Δτ2 determined from the change in duty ratio illustrated in FIG. 8 was approximately 40 seconds. Since the sensor output y2 after the recovering process was 238.4 mV, the actual recovery rate r in the recovering process was 97% according to Equation (1).

Specifically, a higher recovery rate of the gas sensor 200 was obtained with a shorter recovering time and a shorter non-measurement time according to Example 2.

Example 3

Outline of Sensor Element

FIGS. 9A and 9B illustrate a schematic structure of a gas sensor 300 that was subjected to the recovering process according to Example 3. FIG. 9A is a vertical cross-sectional view of a sensor element 301 being a main component of the gas sensor 300 along a longitudinal direction of the sensor element 301 (hereinafter referred to as a "element longitudinal direction"). FIG. 9B is a view including a cross-section of the sensor element 301 vertical to the element longitudinal direction, which is taken along a line C-C' of FIG. 9A.

As the gas sensor 100 according to Example 1 and the gas sensor 200 according to Example 2, the gas sensor 300 determines the concentration of a gas component to be measured in a measurement gas, using a potential difference between the sensing electrode 10 and the reference electrode 20, due to a difference in the concentration of the gas component in the vicinity of the sensing electrode 10 and the reference electrode 20 on the basis of the principle of mixed potential. Furthermore, the gas sensor 300 has the same structure as the gas sensor 200 except for the structure in the gas distribution part at the distal end E1. Thus, the constituent elements of the gas sensor 300 identical to those of the gas sensor 100 or 200 are denoted by the same reference numerals, and the detailed description thereof will be omitted.

The gas sensors 200 and 300 differ in that the sensor element 201 of the gas sensor 200 includes the gas inlet 210 that is opened to the outside and is a two-chamber serial type sensor element, whereas in the sensor element 301 of the gas sensor 300, a first diffusion control part 311 serving as a gas inlet, a buffer space 312, a second diffusion control part 313, a first internal space 314, a third diffusion control part 315, a second internal space 316, a fourth diffusion control part 317, and a third internal space 318 are adjacently formed so as to be in communication with one another in the element longitudinal direction in stated order. The sensor element 301 is a three-chamber serial type sensor element.

The buffer space 312, the first internal space 314, the second internal space 316, and the third internal space 318 are interior spaces provided by hollowing out the fifth solid electrolyte layer 5. The buffer space 312, the first internal space 314, the second internal space 316, and the third internal space 318 are each provided, with its upper portion defined by the lower surface of the sixth solid electrolyte layer 6, its lower portion defined by the upper surface of the fourth solid electrolyte layer 4, and its side portion defined by the side surface of the fifth solid electrolyte layer 5.

Meanwhile, each of the first diffusion control part 311, the second diffusion control part 313, the third diffusion control part 315, and the fourth diffusion control part 317 is provided as two horizontally long slits which are openings longitudinally extending perpendicular to the drawing of FIG. 9A.

The sensing electrode 10 is provided in the third internal space 318 (facing the third internal space 318).

In the sensor element 301, a measurement gas is introduced from the outside space to inside through the first diffusion control part 311 serving as the gas inlet. The measurement gas is given a predetermined diffusion resistance through the first diffusion control part 311, the second diffusion control part 313, the third diffusion control part 315, and the fourth diffusion control part 317, and reaches the vicinity of the sensing electrode 10 after an electrochemical oxygen pump cell whose illustration is omitted adjusts the concentration of oxygen in the first internal space 314, the second internal space 316, and the third internal space 318 so as not to influence the sensing of an unburned hydrocarbon gas.

In the gas sensor 300 having the structure above, the concentration of an unburned hydrocarbon gas in a measurement gas can be determined almost in real time by heating the sensor element 301 to an appropriate temperature using the heater 72 and measuring the potential difference Vs between the sensing electrode 10 and the reference electrode 20. By the continuous use of the gas sensor 300, a gas component or a poisoning substance in a measurement gas is adhered to the sensing electrode 10. Accordingly, the recovering process needs to be performed with appropriate timing to prevent the degradation of the sensor output.

[Recovering Process]

The gas sensor 300 with the structure above was subjected to the recovering process after its use. The gas sensor 300 was used under the following conditions in the normal drive mode, where the initial sensor output y0 was 240 mV and the sensor output y1 before the recovering process was 185 mV;

T0=650° C. (here, the temperature in the vicinity of the sensing electrode 10 was 500° C.); and

D0=20%.

Prior to execution of the recovering process, the recovering temperature T1=1000° C. and the recovering time Δτ1=30 seconds were determined based on the condition setting range RE in FIG. 4. It was previously confirmed that the temperature in the vicinity of the sensing electrode 10 when T1=1000° C. approximately reached 850° C. Besides, condition values of the duty ratio were defined as follows:

D1=75%;
D2=50%; and
D3=1%.

The recovering process was performed under the above conditions according to the procedure illustrated in FIG. 1.

Figure 10:
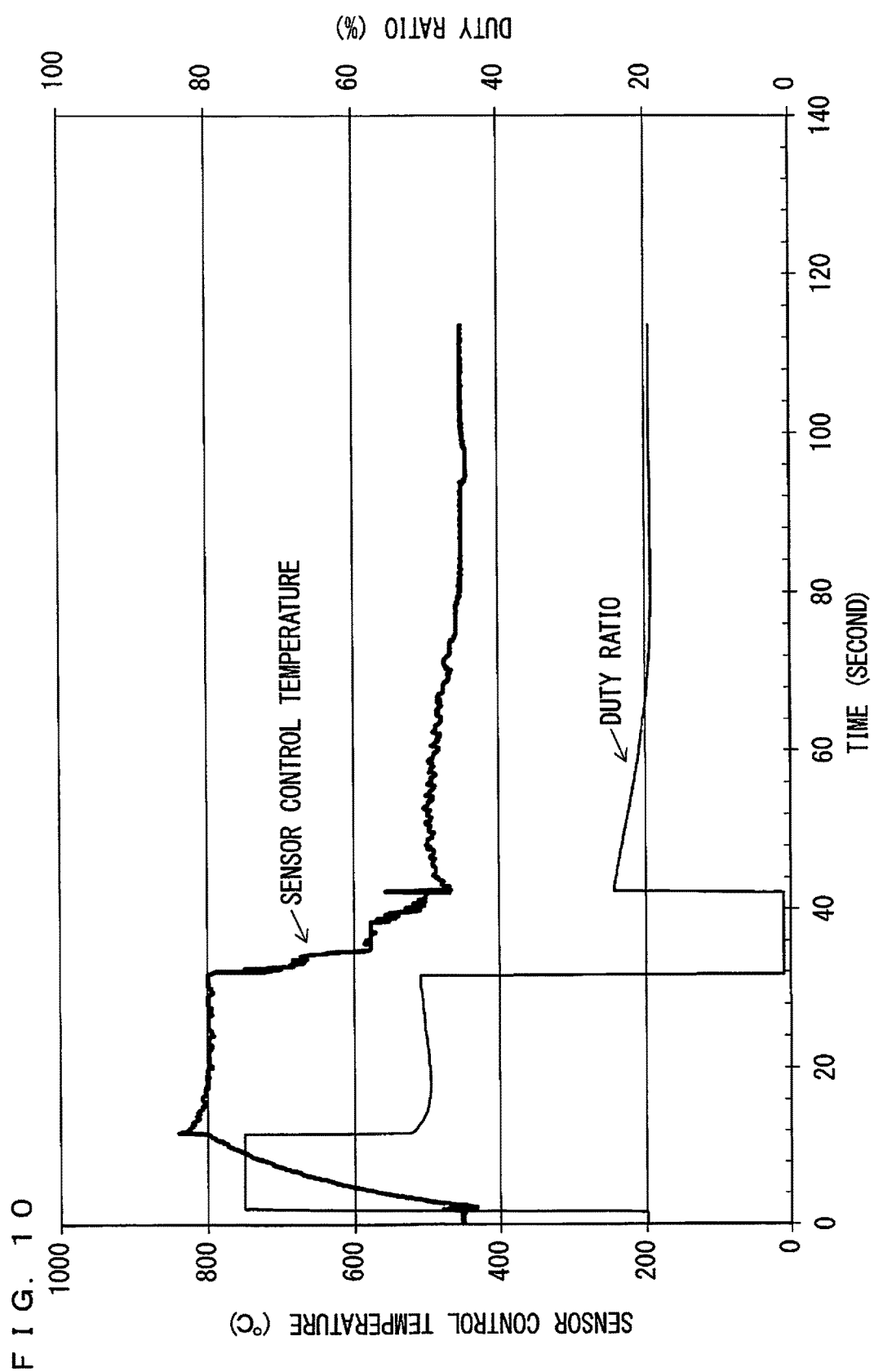
FIG. 10 illustrates a temporal change in sensor control temperature and duty ratio of the gas sensor 300 in the recovering process.

FIG. 10 illustrates a temporal change in sensor control temperature and duty ratio of the gas sensor 300 in the recovering process. The non-measurement time Δτ2 determined from the change in duty ratio illustrated in FIG. 10 was approximately 40 seconds. Since the sensor output y2 after the recovering process was 242.6 mV, the actual recovery rate r in the recovering process was 96% according to Equation (1).

Specifically, a higher recovery rate of the gas sensor 300 was obtained with a shorter recovering time and a shorter non-measurement time according to Example 3.

Example 4

The advantages of repeating the recovering process in the gas sensor 100 according to Example 1 were confirmed. Specifically, with the gas sensor 100 exposed to a degradation atmosphere containing $C_2H_4$=2000 ppm, $O_2$=10%, and $N_2$=a residue, the sensor output of the gas sensor 100 was continuously monitored, and the recovering process was executed approximately every 60 minutes. Then, change in the sensor output was checked. The conditions for the recovering process were the same as those according to Example 1.

Furthermore, as a comparative example, change in the sensor output of a gas sensor which has a structure identical to that of Example and is exposed to the same degradation atmosphere but to which no recovering process is executed was confirmed.

FIG. 11 illustrates a temporal change in sensor output of the gas sensors according to Example and the comparative example. Although the sensor output cannot be normally measured during the recovering process according to Example, the graph is represented by a consecutive line to simplify the illustration.

The result in FIG. 11 confirms that the sensor output observed in the comparative example monotonously decreases over time, whereas the sensor output observed in Example is recovered to approximately 400 mV that is almost in the same level as the initial state every time the recovering process is executed, though the sensor output tends to decrease in-between the recovering processes. The recovery rate r in each of the recovering processes was a value as high as 97% to 98%.

Consequently, the result shows that the sensor output can be recovered many times by repeating the recovering process.

The degradation atmosphere contains a higher percentage of the hydrocarbon gas than that when the gas sensor is actually used. Thus, although the lines representing the degradation in sensor output according to both Example and the comparative example are steeper, the degradation in sensor output when the gas sensor is actually used is less severe than that according to Example in FIG. 11. Thus, the intervals of the recovering process may be sufficiently longer than those of Example, that is, once every approximately 60 minutes.

The invention claimed is:

1. A method for recovering output of a gas sensor including a sensor element by heating said sensor element to a recovering temperature using a heater included in said sensor element, said recovering temperature being a second temperature higher than a first temperature that is a temperature of said sensor element in a normal drive mode, said method comprising the following steps of:
   a) setting said recovering temperature and a recovering time, said recovering time being a time from start of increasing said first temperature up to said recovering temperature until end of maintaining said recovering temperature; and
   b) executing a recovering process based on said recovering temperature and said recovering time that are set in said step a),
   wherein in said step a), said recovering temperature and said recovering time are determined based on a condition setting range previously experimentally identified, said condition setting range being a range in which a recovery rate is expected to be higher than or equal to 95%, said recovery rate being a ratio of a difference in sensor output between immediately after and before said step b) to a difference between a sensor output when said gas sensor starts to be used and said sensor output immediately before said step b), and
said step b) includes the following sub-steps of:
   b-1) heating said sensor element from said first temperature to said recovering temperature at the time when said step b) starts, by setting a duty ratio for said heater to a predetermined value D1 higher than a value in said normal drive mode when said sub-step b-1) starts, and maintaining said value D1 until said sensor element reaches said recovering temperature;
   b-2) maintaining said recovering temperature for a lapse of said recovering time after said sensor element reaches said recovering temperature through said sub-step b-1), by reducing said duty ratio to a value D2 which is not less than 40% of said value D1 and is not more than 80% of said value D1 and performing PID control whose control target value is said value D2;
   b-3) reducing said temperature of said sensor element by reducing said duty ratio to a value D3 lower than said value D2, at the time when said recovering time elapses through said sub-step b-2); and
   b-4) returning said sensor element to a control operation in said normal driving mode at the time when said temperature of said sensor element reaches a value 1 to 1.2 times as high as said first temperature through said sub-step b-3), by instantly changing said duty ratio to a value D0 in said normal drive mode and setting said value D0 to a control target value.

2. The method according to claim 1,
wherein said recovering time is within 1 minute.

3. The method according to claim 1,
wherein said sensor element includes a sensing electrode containing Au, and
said recovering temperature is lower than or equal to a melting point of Au.

4. The method according to claim 1,
wherein 5%≤D0≤30%, 30%≤D1≤100%, and 0%≤D3≤20%.

5. The method according to claim 2,
wherein said sensor element includes a sensing electrode containing Au, and
said recovering temperature is lower than or equal to a melting point of Au.

6. The method according to claim 2,
wherein 5%≤D0≤30%, 30%≤D1≤100%, and 0%≤D3≤20%.

7. The method according to claim 3,
wherein 5%≤D0≤30%, 30%≤D1≤100%, and 0%≤D3≤20%.

8. The method according to claim 5,
wherein 5%≤D0≤30%, 30%≤D1≤100%, and 0%≤D3≤20%.

* * * * *